(12) United States Patent
Mancini

(10) Patent No.: US 8,007,786 B2
(45) Date of Patent: Aug. 30, 2011

(54) RADIOPROTECTIVE SOD SOLUBLE ISOFORM AND USES THEREOF

(75) Inventor: Aldo Mancini, Naples (IT)

(73) Assignee: Asi Agenzia Spaziale Italiana, Rome (IT)

( * ) Notice: Subject to any disclaimer, the term of this patent is extended or adjusted under 35 U.S.C. 154(b) by 0 days.

(21) Appl. No.: 12/581,980

(22) Filed: Oct. 20, 2009

(65) Prior Publication Data

US 2011/0091438 A1    Apr. 21, 2011

(51) Int. Cl.
*A61K 38/44* (2006.01)
*C12P 1/00* (2006.01)

(52) U.S. Cl. ........................ 424/94.4; 435/267

(58) Field of Classification Search .............. 424/94.4; 435/267

See application file for complete search history.

(56) References Cited

OTHER PUBLICATIONS

Borrelli et al. (2009), Free Radical Biology and Medicine 46: 110-116.*
Epperly et al. (2001) Int. J. Cancer 96: 221-231.*

\* cited by examiner

*Primary Examiner* — Tekchand Saidha
(74) *Attorney, Agent, or Firm* — Lucas & Mercanti, LLP

(57) ABSTRACT

The invention refers to a specific isoform of MnSOD (Mn-superoxide dismutase) and its uses for protecting and curing subjects exposed to radiations, specifically space radiations.

Figure 1:
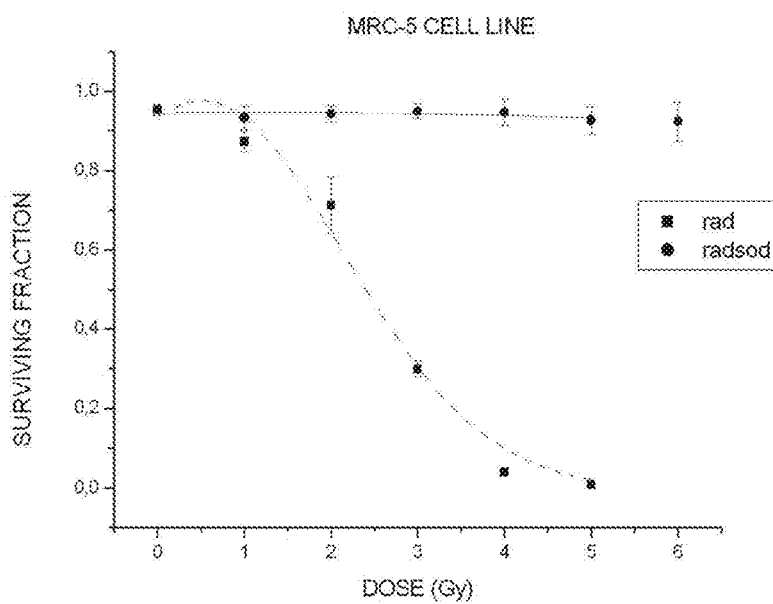

17 Claims, 6 Drawing Sheets

# RADIOPROTECTIVE SOD SOLUBLE ISOFORM AND USES THEREOF

FIELD OF THE INVENTION

The invention refers to a specific isoform of MnSOD (Mn-superoxide dismutase) and its uses for protecting and curing subjects exposed to radiations, specifically space radiations.

BACKGROUND

Organisms exposed to ionizing radiations are mainly damaged by free radicals, which are generated by the radiolysis of water contained in the cells.

The superoxide dismutase (SOD) family of proteins is necessary to protect oxygen-utilizing cells from the toxicity of the reactive oxygen species (ROS) produced during normal metabolism. Besides being protective proteins, these enzymes are also key components of signalling pathways that regulate cell physiology. SODs catalyze the reaction: with hydrogen peroxide being then removed by catalases (CATs) and peroxidases, of which glutathione peroxidase (GPx) has been the most widely studied. There are three known forms of SOD in mammalian cells: a copper- and zinc-containing superoxide dismutase (CuZnSOD) found mainly in the cytoplasm and in the nucleus, a manganese-containing superoxide dismutase (MnSOD) found in the mitochondria, and an extracellular superoxide dismutase (ecSOD) found primarily in the extracellular compartments. The superoxide dismutase are enzymes of remarkable pharmacological interest for their potential role in the prevention of all pathologies involving oxidative damage. It has been recently proposed that these enzymes can be useful in the prevention and in the treatment of damages caused by physical agents and, particularly by ionizing radiations (1) which generate high levels of free radicals (2-6).

The large scientific and practical interest toward MnSOD has resulted in intensive developments of new technologies for its production but, despite great efforts, efficient production of recombinant human SOD in prokaryotic systems or simple eukaryotes failed. This failure has so far hindered its large-scale production and protein genetic engineering (7). Recently a new technology for radio-protective gene therapy using the transgene for the antioxidant manganese superoxide dismutase, delivered to specific target organs (lung, esophagus, oral cavity, oropharynx, and bladder) using gene transfer vectors including plasmid/liposomes (PL) and adenovirus was developed. Significant reduction of organ specific tissue injury has been demonstrated in several organ systems in rodent models.

Moreover, the application of MnSOD-PL gene therapy in the setting of fractionated chemo-radiotherapy is being tested in clinical trials for the prevention of esophagitis during the treatment of lung non-small-cells carcinoma, and in the prevention of mucositis during combination therapy of carcinomas of the head and neck. Encouraging results in pre-clinical models have suggested that radioprotective gene therapy may facilitate dose escalation protocols to allow increases in the therapeutic ratio of cancer radiotherapy (8).

Recently a significant reduction of tissue injury from irradiation damages was demonstrated by using the MnSOD-plasmid/liposome treatments in the protection of murine lung.

DESCRIPTION OF THE INVENTION

The author of the instant invention have shown that a new active recombinant human MnSOD (rMnSOD; disclosed in Mancini et al. Int J. Cancer 119; 932-943, 2006 and in WO03/072768), easily administrable in vivo, exerts the same radioprotective effect on the normal cells and organisms as any MnSOD, and it is also radio-sensitizing for tumour cells (Borrelli A., et al. Free Radic Biol Med. 2009 46:110-6). rMnSOD has the following aa. sequence (Swiss Prot. Acc. No P04179; SEQ ID No. 1):

MLSRAVCGTSRQLAPALGYLGSRQKHSLPDLPYDYGALEPHINAQIMQ

LHHSKHHAAYVNNLNVTEEKYQEALAKGDVTAQIALQPALKFNGGGHI

NHSIFWTNLSPNGGGEPKGELLEAIKRDFGSFDKFKEKLTAASVGVQG

SGWGWLGFNKERGHLQIAACPNQDPLQGTTGLIPLLGIDVWEHAYYLQ

YKNVRPDYLKAIWNVINWENVTERYMACKK.

No data are available on the protective effect on radiations present in the atmosphere and more general in the space, as ionizing and protonizing radiations. Authors here show how healthy animals, exposed to lethal dose of ionizing and protonizing radiations and daily injected with rMnSOD, resulted protected by radio-damages and were still alive 30 days after the irradiation. Animals treated with only PBS solution, while in the absence of rMnSOD, died after 7-8 days from the radio-treatments. The molecular analysis of all irradiated tissues revealed that the anti-apoptotic AVEN gene (UniProtKB/Swiss-Prot: AVEN_HUMAN, Q9NQS1) is activated only in the animals treated in the presence of rMnSOD. The data suggest that rMnSOD deserves to be considered as a pharmaceutical tool to make radiotherapy more selective on cancer cells and to prevent and/or cure the accidental damages derived by the exposure to ionizing and protonizing radiations.

Authors show the radio-protective role of a specific isoform of a human recombinant protein (rMnSOD) which possesses the specific SOD antioxidative and antiradical activity and which can be easily administrated in vivo through the systemic pathway, reaching and penetrating into the cells, without require any additional manipulation (9,10).

rMnSOD effects were studied in vitro, on irradiated normal and cancer cells, and in vivo, on normal C57BL/6J mice exposed to lethal doses of ionizing radiations.

The results demonstrated that rMnSOD exerts a radio-protective effect on normal cells (in vitro) and on normal tissues (in vivo) while it is radiosensitizing for cancer cells (in vitro). Moreover, while the animals treated in the absence of rMnSOD would survive no longer than 6-7 days after radiations, those treated with rMnSOD survived for a much longer period up to 30 days considered as the experimental time point.

Therefore it is an object of the instant invention a method for protecting a subject from exposure to radiations comprising the administration of an effective protective amount of rMnSOD of SEQ ID No. 1, or functional fragments thereof. Preferably the rMnSOD is administered in an amount from 0.08 g/Kg body weight to 0.1 g/Kg body weight for at least 30 days before the exposure to radiations.

In a preferred embodiment said radiations are space radiations.

In another preferred embodiment said radiations are sun radiations.

In another preferred embodiment said radiations are from depleted uranium.

In another preferred embodiment said radiations are from anti-tumoral metabolic therapies administration of radioactive isotopes or radiating therapies. Such application is particularly useful for protecting the kidney parenchyma of subjects treated with radio-sotopes and for protecting from skin burns and ulcers.

In another preferred embodiment said radiations from radioactive isotopes for radio-diagnostics.

In another preferred embodiment said radiations are ionizing and/or protonizing radiations.

It is another object of the invention a method for treating a subject exposed to radiations comprising the administration of an effective therapeutically active amount of rMnSOD of SEQ ID No. 1. or functional fragments thereof. Preferably the rMnSOD is administered in an amount from 0.08 g/Kg body weight to 0.1 g/Kg body weight for at least 30 days after the exposure to radiations.

In a preferred embodiment said radiations are space radiations.

In another preferred embodiment said radiations are ionizing and/or protonizing radiations.

FIGURE LEGENDS

FIG. 1 The cell strains were treated in the presence of rMnSOD (0-1.5 µM). 1 days after irradiation, the cells were detached with Trypsin-EDTA, and plated at a concentration of 200 cells/dishes in drug-free medium. Fourteen days later the colonies were fixed and counted by using a crystal violet staining to evaluate the number of colonies present in the dishes.

Figure 2:
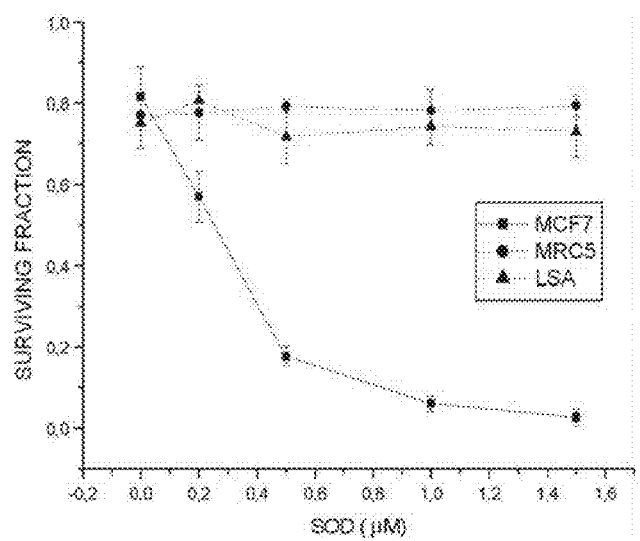

FIG. 2 On the MRC-5 normal cells the sole irradiation induces a dose-dependent radiodamage that with 3 Gy of X-rays leads to the death of cells (rad). The same radiotreatment, in the presence of 0.5 µM rMnSOD, results in a significant radioprotection and survival of cells(rad+sod).

Figure 3:
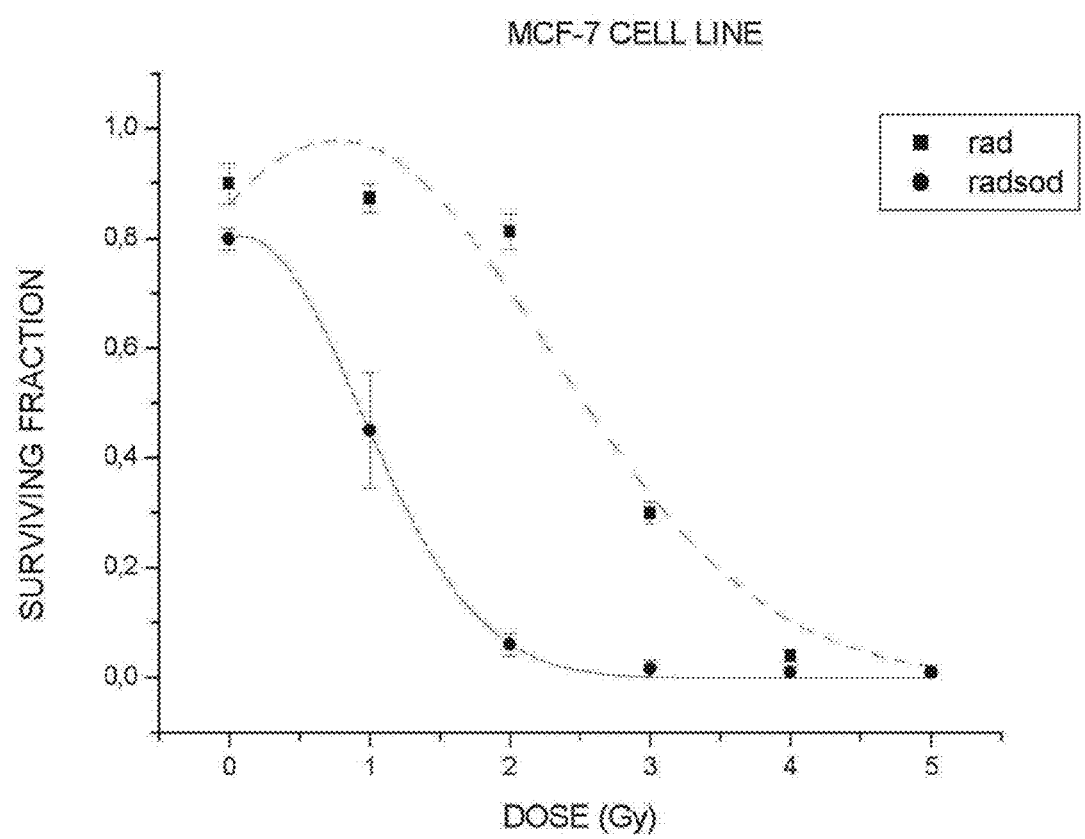

FIG. 3 On the MCF-7, the sole radiation with 3 Gy of X-rays (rad) led to the death of the cells after 14 days, whereas the same cells are killed when they are irradiated with 2 Gy and in the presence of 0.5 µM rMnSOD(rad+sod).

Figure 4:
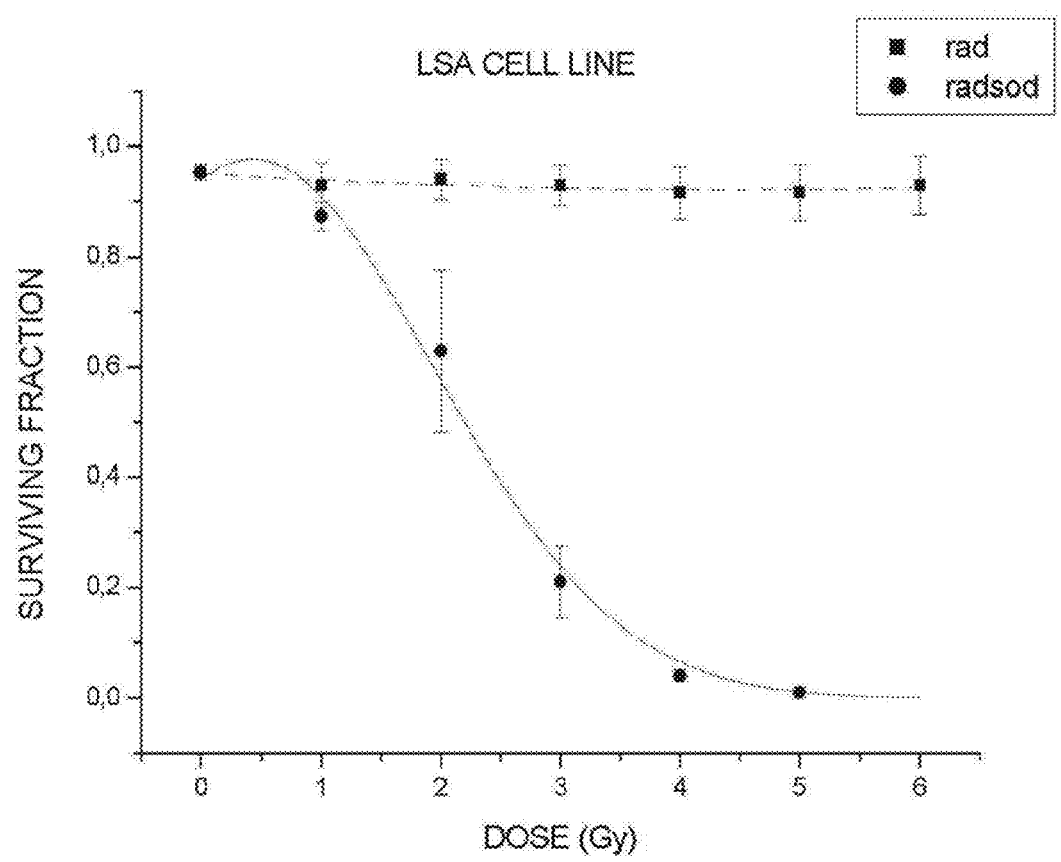

FIG. 4 On the LSA cells, the sole irradiation with 6 Gy of X-rays (rad) do not effect the cell survival of LSA cells (rad). On the contrary, when the LSA cells are irradiated with only 3 Gy, in the presence of 0.5 µM rMnSOD, the cells are killed (rad+sod).

Figure 5:
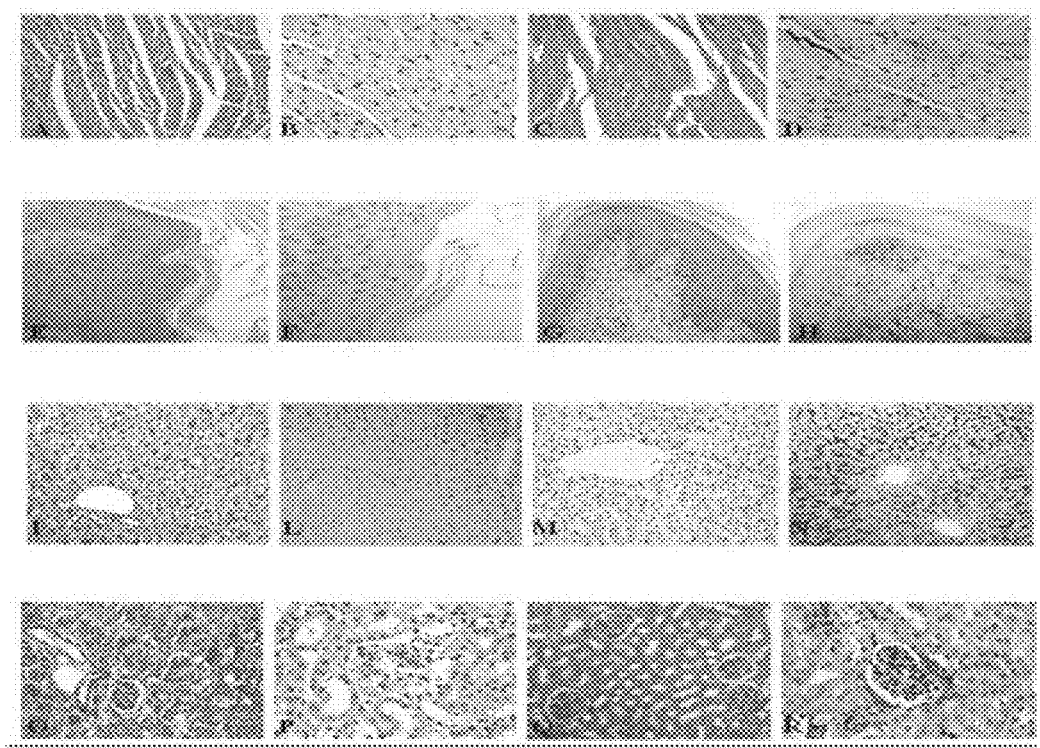

FIG. 5 (A-R) Histologic sections of organs of normal mice underwent to a lethal dose of ionizing radiations, treated in the presence or in the absence of rMnSOD Heart: the histological examination revealed that in the heart of mice which didn't receive the rMnSOD, were present intensive areas of miofibrillolisis and a hydropic degeneration (A), ×250, and the absence of endogenous expression of rMnSOD at the immunochemical evaluation (B)×250. On the contrary, in the hearts of animals treated in presence of rMnSOD, the tissue integrity was clear (C)×250, and rMnSOD was strongly represented in the interstitial space, at immunochemical detection (D)×250 Cervix uteri: the histological examination revealed that in the cervix uteri of mice which didn't receive the rMnSOD, were present intensive areas of structural discontinuity (E)×250, and the absence of endogenous expression of rMnSOD at the immunochemical evaluation (F)×250. On the contrary, in the cervix uteri of mice treated in presence of rMnSOD, the tissue integrity was clear (G)×250, and was also evident the presence of rMnSOD in the cytoplasm and in the interstitial space, at immunochemical detection (H)×250 Liver: The lobulo-laminar structure resulted preserved both in the control (I) and in the treated section (L). The positive immunochemical reaction has been evident either in the sinusoid that in the hepatocytes cells, particularly it is evident the positivity of the membrane, (M) with high increasing in the treated animals (N)×250. Kidney: the histological examination revealed that in the kidney of mice which didn't receive the rMnSOD, showed a glomerular coarctation and tubular degeneration (O)×250, and the absence of endogenous expression of rMnSOD at the immunochemical evaluation (P)×250., while the animal's kidneys treated in presence of rMnSOD, a total integrity of the structures (Q)×250, with an ubiquitous presence of rMnSOD in the interstitial space, at immunochemical detection (R)×250. The quantitative evaluations of immunochemical reaction were obtained by using an imaging analyzer Leica50.

Figure 6:
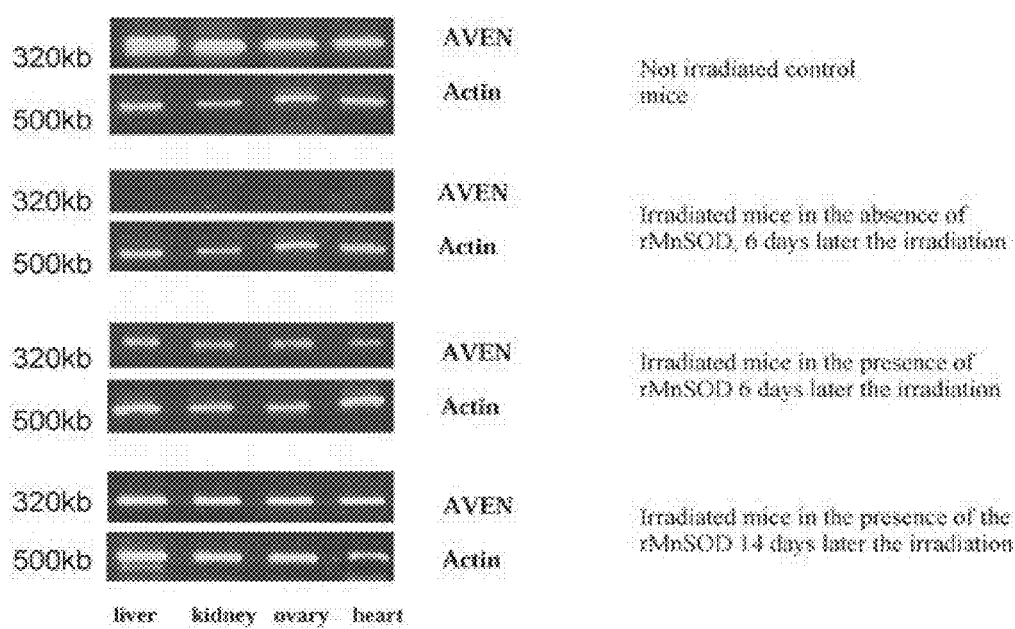

FIG. 6 AVEN expression in irradiated mice in the presence or in the absence of rMnSOD. The figure showed the amplified fragments of AVEN gene (352 bp) in the different experimental groups. Three groups of inbreed C57BI 6 mice were used in PCR experiments. The first group was of untreated control animals; the second group received high lethal dose of ionizing radiations and at the third group was treated before irradiation 0.08 mg/Kg/die, for 15 days of in the presence of recombinant rMnSOD. The actin transcripts (500 bp) was shown as control of cDNA quantity (inferior line).

Figure 7:
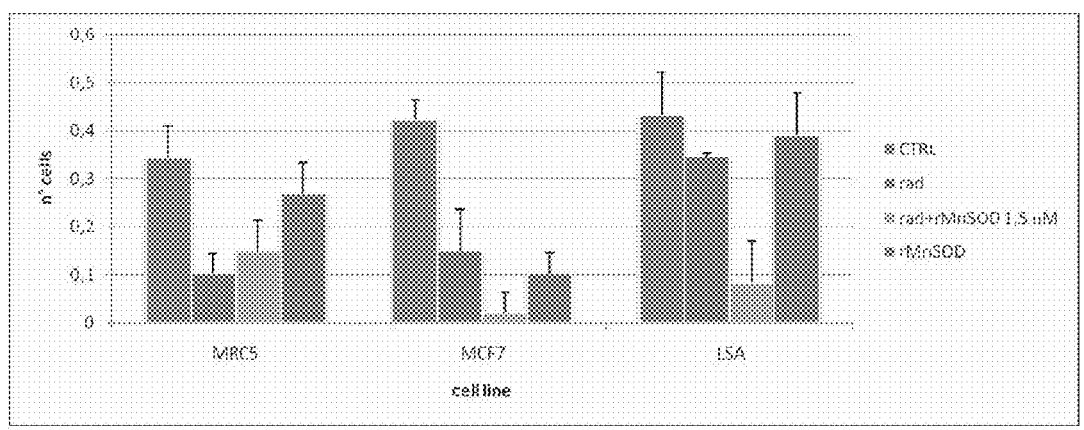

FIG. 7 Target cells, in three independent experiments, were exposed to radiations by a proton beams having an energy of 62 MeV with a dose of 6 Gy. On the normal cells (MRC-5) the killing effect of the sole radiations resulted of 67% of the cell death, but when the same cells were irradiated in the presence of rMnSOD, 86.9% of them survived to radio-treatment. On tumor cells, the sole proton beams produced a killing effect of 34% for MCF-7 cells and 29% for LSA cells. On the contrary, when these tumor cells were irradiated in the presence of rMnSOD the killing effect was of 96% for MCF-7 cells and 56% for LSA cells.

MATERIALS AND METHODS

Enzymes rMnSOD was obtained as previously described (9), while its enzymatic activity evaluated according to McCord and Fridovich (11). Commercial Cu/Zn-SOD was from SIGMA.

Cell Cultures

The cell lines investigated here (MCF-7, MRC-5) are described and available from ATTC (MCF-7: cat. n° HTB-22™; MRC-5: ca. n° CCL-171™). Cells were grown in Dulbecco's modified Eagle's medium supplemented with 5% of fetal bovine serum (FCS) at 37° C. in a humidified atmosphere containing 5% of $CO_2$. The culture medium was replaced every 3-4 days. The liposarcoma-derived cell line (LSA) was obtained and cultured as previously described (12; WO03/072768; DSMZ n. 2029).

Clonogenic tests on cells following X-rays treatment in the presence or in the absence of rMnSOD Confluent 75 cm2 flasks of cells were trypsinized, counted with a haemocytometer and diluted in complete media to obtain 100 cells mL. Two mL of cell suspension was plated in each well of a 6 well tissue culture plate to obtain 200 cells per well. For each cell line used in the present experiments were performed, in triplicate, clonogenic tests on four different cells groups:

A: CTRL as cells cultured in their specific medium and considered as negative control B: SOD as cells treated in the presence of the sole rMnSOD to determine the effect of rMnSOD on clonogenic survival. The cells were treated with different concentration of rMnSOD (0-1.5 µM), trypsinized after 24 h and plated in drug-free medium.

C: RAD as cells irradiated in the absence of rMnSOD to determine the effect of radiation on clonogenic survival. The cells were irradiated (0-6 Gy) with X photons generated by a linear accelerator Philips SL 75 having nominal acceleration potential of 6 MV, and with 42, 127 U/Monitor and a dose-rate of 300 cGy/min.

D: RAD+SOD as cells irradiated in the presence of rMnSOD to determine the effect of combination treatment on clonogenic survival.

In the clonogenic tests to evaluate the effect of the sole rMnSOD on the normal or tumoural cells, it was noted that the concentration of 0.5 µM of rMnSOD is the concentration of which were not observed any harmful effects on the cell lines used. So to test the radiosensitizing or radioprotective effect of rMnSOD was chosen precisely the concentration of 0.5 µM.

The cells were treated with 0.5 µM rMnSOD for 24 h, irradiated and plated after 1 h. Colonies were stained with crystal violet after 14 days and those containing at last 30 cells were counted as surviving colonies. The plating efficiency and the survival fraction, for each cell line after each treatment, were calculated according to the method proposed by Franken (13) averaged approximately 80% for all cell lines. Survival was calculated in comparison to non-irradiated samples using an average of three determinations for the same dose-rate to cells (±SE). The surviving fraction of cells following the above mentioned dose of X-rays exposure, was used as a measure of cell sensitivity to X-rays and radioprotection of rMnSOD. In particular, the surviving fraction at a fixed X-rays exposure was used as a measure of cell sensitivity as several reports indicate that the clonogenic survival of cells at a fixed dose (usually 2 Gy of ionizing radiation) is a single parameter of the survival curve that correlates well with cell sensitivity (14-18).

The surviving fraction of cells following 0 to 6 Gy/min was able to discriminate between the radio-sensitivity of normal and cancer cells (19,20). Average values with standard deviation were determined from 3 independent experiments using different rMnSOD preparations.

Animals Treatment

Thirty-five female C57BL/6J mice, from Charles River, were used for all experimental procedures. Fifteen of them were divided into three groups of five animals each.

The first (1st) group was exposed to a lethal dose of ionizing radiations, achieved by using X-ray generated by a Linac (Philips SL 75) with a nominal potential of 6 MV and a dose-rate of 300 U.M./min. The mice were put in a dedicated phantom (21×30×35 cm3) and were irradiated with an isocentric technique. The prescription dose to mice (6 Gy) was delivered with two opposing fields (30×25 cm2), at source-phantom distance of 89.5 cm and depth of 10.5 cm. It was estimated, for each mouse, a minimum dose (at skin) of 5 Gy and a maximum dose (at mouse mid-line) of 6.3 Gy. Immediately after the radio-treatments, mice of 1st group were treated in the presence of 0.08 mg/kg rMnSOD in 100 µl PBS while the 2nd group received a daily injection of PBS. The 3rd group of animals did not receive the irradiation but was injected in the presence of 100 µl PBS. All animals were maintained in the standard feeding condition and with a cycle of dark and light. Seven days later the mice were sacrificed through cervical dislocation and their organs were examined in search of structural modifications and for the detection of the rMnSOD by immunochemical analysis. The other twenty animals were divided into four groups of five each. The first group received irradiation only, the second group received irradiation plus rMnSOD, the third group received rMnSOD only and the fourth group received only PBS. The animals were used to evaluate their survival after being exposed to ionizing radiation, in the presence or in the absence of rMnSOD. The observation of animals continued until 30 days that was considered as the experimental time point.

RNA Extraction 50 mg of tissue derived from liver, kidney, ovary and heart of experimental C57BI/6 mice exposed to ionizing radiations was used for total RNA extraction (RNAzol, Invitrogen) (21) according to the manufacturer's instructions and the integrity of all tested total RNA was verified by agarose gel electrophoresis.

Reverse transcription: 2 µg of total RNA in a final volume of 20 µl was reverse-transcribed by Avian myeloblastosis virus (AMV) reverse transcriptase (Gibco BRL-Invitrogen) according to manufacturer's instruction in presence of random examer primers at 37° C. per 60 min.

PCR Amplification

PCR analysis of AVEN gene expression was performed by using a Gene Amp PCR system 9700 (Applied Biosystem) with Taq Gold (Applera) and mouse sequence-specific primers. Actin was used as housekeeping control gene. The primer used were:

```
                                          (SEQ ID No. 2)
    Aven Fw GAA TCT CAG CGG GGC ACA G;

(SEQ ID No. 3)
    Aven Rw GGG CAA GCA CCA GCA GCA G.

(SEQ ID No. 4)
    Actin Fw GAC TAC CTC ATG AAG ATC CT;

(SEQ ID No. 5)
    Actin Rw GCT TGC TGA TCC ACA TCT GC.
```

The PCR condition was: initial denaturation at 95° per 10 min followed by 36 cycles: 95°, 45"; 58°, 45" and 72° 45" with a final extension at 72° per 10 min.

The amplification products were run on 1% agarose gel in 0.5×TBE (Tris Borate EDTA) buffer for the control of the amplicons length.

Histology and Immunocytochemistry

Light Microscopy and immunochemical determinations were performed according to the methods previously described (9). The quantitative evaluation of the immunochemical determinations was obtained by using an Imaging Analyzer Leica Q50.

Statistical Analysis

Data obtained from the clonogenic tests on all cell lines (MCF-7, MRC-5, LSA) in two different condition: irradiated in absence (rad) and in the presence of rMnSOD (rad+sod), were statistically analysed by using the linear-quadratic (LQ) formulation e-($\alpha$D+$\beta$D2) as model of biological response to radiation.

Results

Clonogenic Assay of Cells Irradiated in the Presence or in the Absence of rMnSOD The biological effect of the sole rMnSOD on MRC-5 cells produces only a low inhibition of their growth rate, suggesting that rMnSOD at 0.5 or 1.5 µM is poorly toxic for normal cells. (FIG. 1), while the exposure to ionizing radiations of MRC-5 cells, in the absence of rMnSOD resulted in the 90% of cell death. On the contrary, 80% of these cells, irradiated in the presence of rMnSOD, survived to radio-treatment and 14 days later, many colonies were counted (FIG. 2).

In the test performed on MCF-7 cells, to kill all cancer cells with the sole rMnSOD, was enough a dose of 1.5 µM (FIG. 1), and with the sole radiations, the killing effect was obtained with 5 Gy. (FIG. 3). The same result was reached by irradiating the cells in the presence of 0.5 μM and 3 Gy of X-rays (FIG. 3).

On the LSA cells was not found any damage when the cells were treated with the sole protein (FIG. 1) or with the sole radiations (FIG. 4), but a rapid mortality of LSA cells was observed when the cells were irradiated with a dose of 3 Gy and in the presence of 0.5 μM rMnSOD (FIG. 4).

Statistical Analysis

The statistical analysis of the clonogenic tests on the cell lines underwent to irradiation in the presence or in the absence of rMnSOD by using the linearquadratic (LQ) formulation $e^{-(\alpha D+\beta D2)}$ as model of biological response to radiation, was significant and allowed the determination of the α/β ratio for all treated cells lines. By these data it is possible to observe that rMnSOD exerts a radiosensitizing effect on the MCF-7 and LSA cells, while for the MRC-5 cell line the rMnSOD provides a radio-resistance ($\alpha/\beta_{radsod} < \alpha/\beta_{rad}$) (Table II).

TABLE II

|  | $R^2$ | α | β | α/β |
|---|---|---|---|---|
| MCF-7 cells | | | | |
| Rad | 0.969 | −0.33 ± 0.18 | 0.21 ± 0.07 | −1.5 ± 0.9 |
| Rad + rMnSOD | 0.999 | −0.13 ± 0.11 | 071 ± 0.10 | 0.2 ± 0.2 |
| MRC-5 cells | | | | |
| Rad | 0.985 | −0.19 ± 0.11 | 0.19 ± 0.04 | −1.0 ± 0.6 |
| Rad + rMnSOD | 0.536 | −0.03 ± 0.007 | 0.0011 ± 0.0011 | −3 ± 7 |
| LSA cells | | | | |
| Rad | 0.709 | −0.014 ± 0.006 | 0.0016 ± 0.0010 | −9 ± −7 |
| Rad + rMnSOD | 0.993 | −0.18 ± 0.08 | −0.21 ± 0.03 | −0.8 ± 0.4 |

Radio-treatments of Healthy Animals in the Presence or in the Absence of rMnSOD

After radio-treatment each animal of the test group (3rd), received an intraperitoneal injection (i.p) of rMnSOD (0.08 mg/kg), and the injections continued for 6 additional days. The control group (2nd) received only an equal volume of PBS i.p. At the histological analysis, the selected organs (Heart, Cervix uterus, Liver and Kidneys) of animals treated in the presence of rMnSOD, did not show signs of radio-damages. The presence of rMnSOD in the animal's tissues exposed to radio-treatments was detected and quantified, by immunochemical analysis, using an imaging analyzer Leica Q50. The presence of rMnSOD was only observed in the interstitial spaces of the animal's tissues who underwent radiotreatment in the presence of rMnSOD. On the contrary, the control mice, which did not receive rMnSOD injections, showed clear signs of radio-necrosis, and their tissues were found free of rMnSOD in the interstitial space (FIG. 5 A-R). Moreover, in parallel experiments, 80% of animals irradiated and daily treated in the presence of rMnSOD, (0.08 mg/kg) were still alive after 30 days from the radio-treatment, considered as the time point of experiment, while the control group irradiated in the absence of rMnSOD died after 6-7 days from the radiotreatment (Table I).

The quantitative analysis of the immunochemical localization of rMnSOD in the animal's tissue irradiated in the presence or in the absence of rMnSOD was correlated to its radioprotective effect. The differences in radioprotection on animals between rMnSOD and mock-treated groups of mice were assessed using the Fisher's exact test (p<0.02).

TABLE I

|  |  | % Positive Stromal cells | % Positive Parenchimal cells | Statistic evaluation on 50 areas |
|---|---|---|---|---|
| Heart | Control | 2% | 3% | P > 0.001 |
|  | Treated | 25% | 30% |  |
| Kidney | Control | 6% | 10% | P > 0.005 |
|  | Treated | 6% | 40% |  |
| Liver | Control | 6% | 10% | P > 0.001 |
|  | Treated | 60% | 80% |  |
| Cervix Utery | Control | 1% | 2% | P > 0.001 |
|  | Treated | 60% | 40% |  |

AVEN Expression in Irradiated Mice in Presence o in the Absence of rMnSOD

The Aven anti-apoptotic gene was found constitutively activated in the healthy animals who did not receive any kind of treatments. In the group of animals who underwent to lethal doses of X-rays, in the absence of rMnSOD, the Aven gene was found completely switched off and their organs structurally degenerated. On the contrary, at the 7th day of treatment the Aven gene expression was decreased in the animal's organs who were treated with rMnSOD, following the lethal dose of X-rays. However after 14 days from irradiation, the gene resulted fully active, indicating that the radio-damage was recovered (FIG. 6).

The data presented show that rMnSOD, a specific human recombinant isoform of Manganese Superoxide Dismutase liposarcoma derived, produces a radio-protective effect on normal cells while it is radio-sensitizing for cancer cells, both in vitro and in vivo. In particular, we have observed that the exposure to ionizing irradiation of human normal fibroblasts (MRC-5 cell line) with different doses of X-rays, have point out that the radio-damages were dose dependent (as expected) and that the 3 Gy of X-rays could be sufficient to kill cells after 14 days from irradiation. The same cells, grown in the presence of the sole rMnSOD, at a growing concentrations, until the maximal dose of 1.5 μM/100 μl PBS, did not influence negatively on the cell growth in the clonogenic test. On the contrary, when the same cells were exposed to lethal dose (6 Gy) of X-rays and in the presence of 0.5 μM/100 μl PBS rMnSOD, the cells were clearly protected from radio-damage.

On the tumor cells the effect of rMnSOD was radio-sensitizing. Indeed, while for the MCF-7 cells, the killing effect with the sole radiation was reached with 4 Gy, or with the sole rMnSOD with 0.5 μM/100 μl PBS. The same significant killing effect was obtained by the exposure of these cells with only 2 Gy of ionizing radiations, and in the presence of only 0.5 μM/100 μl PBS.

Also in the case of liposarcoma, the same radio-sensitizing effect of rMnSOD was observed, although with some difference that reflects the characteristic radioresistance of liposarcoma. On these cells the sole lethal dose (6 Gy) of x-rays or the sole maximal dose of rMnSOD, i.e. 1.5 μM/100 μl PBS, not have the slightest impact on the cell growth and therefore their survival.

On the contrary, when the LSA cells were irradiated with only 3 Gy of X-rays and in the presence of 0.5 μM/100 μl PBS rMnSOD, a significant killing effect was registered, thereby indicating that the protein has a clear radio-sensitizing role on the cancer cells tested.

Although have been used only two cancer cell lines, the fact that ionizing radiations produce free radicals in all the cells, suggests that the rMnSOD could be useful to amplify the radio-damage effect for all kind of cancers.

Moreover, the conviction that it is precisely the rMnSOD to provide radioprotection or radio-sensitizing, derives by the observations that when it was used a commercial SOD or a thermal inactivated rMnSOD both the effects were not highlighted.

Both the observed effect, respectively, on the normal and tumoural cells could have a common molecular base which was previously discussed (9,10). Briefly, it is being linked to the fact that in cancer cells, unlike normal cells, are produced limited amounts of catalase (22,23) which converts hydrogen peroxide into molecular oxygen. Since ionizing radiations, as indeed any other anticancer molecule, induce the production of high levels of free radicals both in normal cells and in cancer cells, the threshold of toxicity will be achieved more easily in cancer cells than in normal ones and thus leading tumor cells to apoptosis (10).

The presence of rMnSOD in the irradiated cells might create an oxidative difference that leads to preferential inhibition of cell proliferation and increases cell death in cancer cells. Such mechanism seems to be very promising since it could foresee a therapeutic use of rMnSOD to amplify the effect of anticancer radiotherapies, especially in the case of radio-resistant tumours like liposarcoma and, at the same time, to reduce their dose-rate.

Further the study was extended to investigate if the radio-protective effect of rMnSOD is obtained also when the cells are exposed to proton beams, in the presence or in the absence of the rMnSOD. Thus normal (MRC-5) and tumoral (MCF-7 and LSA) cells were exposed to 62 Mev equivalent from proton beams. The results clearly indicated that the rMnSOD provide the same selective effect also in the case of proton beams (FIG. 7). Such protection is of relevance as protective and therapeutic means of subjects exposed to space radiations.

Radio-protective and radio-sensitizing effects of MnSOD have already been reported by using molecular medicine and gene-therapy methods (24-28). However prior art cases require methods necessitating the manipulation of the MnSOD, to get the molecule into the cells. In the case of the rMnSOD used in the instant invention, the protein is easily administrable in vivo, and does not require any prior manipulation. This is an undoubted advantage for therapeutic applications.

The radio-protective effect of rMnSOD was also studied in vivo. Animals exposed to lethal doses of X-rays and daily injected with 0.08 mg/kg rMnSOD resulted protected by the damages generated by ionizing radiations. The animal's organs irradiated in the presence of rMnSOD showed an high and statistically significant concentration of rMnSOD at the interstitial spaces level that was absolutely absent in the animals who did not receive the rMnSOD treatment following the ionizing radiation. Moreover, in all of animals which did not receive the rMnSOD, the organs resulted completely degenerated, leading to animals death after only 7-8 days from the radio-treatments. On the contrary, animals who received the rMnSOD treatment were still alive 30 days after the radiation. Also in these cases, the thermally inactivated rMnSOD or the commercially available SOD (Sigma) used as control, did not show the same radio-protection effect or survival rate. These data suggest that rMnSOD might protect the mitochondria thus contributing to maintain their integrity. This hypotheses, is indeed strongly supported by the results obtained by molecular analysis of the expression of the anti-apoptotic Aven gene in all the examined animal's tissues. The Aven gene was actively expressed in control animals that had not undergone radiating treatment, while it appeared completely switched off in those animals irradiated in the absence of rMnSOD. In the animals irradiated in the presence of rMnSOD, the Aven gene was partially inactivated up to the 7th day after the irradiation. However, after 14 days, the Aven gene turned to be fully active, suggesting that the damaged tissues were completely restored, and that rMnSOD provided protection of the normal cells by inhibiting the apoptotic pathway, and it is appropriate to point out that these data also agree with that one observed in vitro, on normal fibroblasts. The product of the Aven gene binds the cytochrome-c released by the injuried mitochondria during apoptosis. A high amount of cytochrome-c inactivates the Aven gene facilitating the caspases activation, which in turn will lead damaged cells to death (29-32). Then rMnSOD provides a protective effect by inhibiting the inactivation of the Aven gene, and more probably by shielding the mitochondria from radio-damages, inhibiting cytochrome-c release.

By considering the enzymatic nature of rMnSOD, usually confined into the mitochondrial matrix, we believe that this latter hypotheses could be more reasonable, although it has not yet been well investigated and not yet clarified. The use of a single and lethal dose radiation in experiments on animals is certainly restraining and does not allow us to understand exactly the limits within which rMnSOD exerts its radio-protective effect or its radio-sensitizing one in cancer cells. Notwithstanding, we believe that the enhanced survival of the animals treated was due to the sole rMnSOD. Therefore, among the several observed radioprotection structural, ultrastructural or molecular indicators, both in vitro and in vivo, the one related to the survival of animals exposed to lethal dose of x-Rays is the most convincing. A further study on a large population of animals is, however, necessary. New experiments will have to test, for instance, the effects of larger doses of ionizing radiations and rMnSOD, as we have done with the in vitro experiments. At the same time, it will also be necessary to extent the investigation rMnSOD's radioprotection effect on all the wide range of ionizing radiations, included those produced by protons and heavy ions, which are particularly present in the cosmic space and in our lab we are currently working on such topics.

In conclusion, the data presented clearly indicate that the rMnSOD provides a radio-protection for normal cells and confirm also the previous observations of a radio-protective effect of MnSOD proposed by others researches. At the same time, the rMnSOD was radio-sensitizing for tumour cells, and both the effects resulted statistically significant. Such data could lead to direct applications in clinical practice, especially because the molecule does not require any manipulation to be safely injected into organisms, its therapeutic potentiality, as well as the possibility to prevent the damages generated by exposure of normal cells to ionizing radiations, indicate that the rMnSOD deserves to be considered as a tool to amplify the effects of cancer radio-therapy, increasing their specific and selective effect on cancer cells and, at the same time to provide a protection to the organism daily or accidentally exposed to ionizing radiations.

BIBLIOGRAPHY

1) Epperly, M. W.; Gretton, J. E.; Sikora, C. A.; Jefferson, M.; Bernarding, M.; Nie, S.; and Greenberger, J. S. Mitochondrial localization of superoxide dismutase is required for decreasing radiation cellular damage. Radiat Res; 160: 568-578; 2003
2) Valko, M.; Rhodes, C. J.; Moncol, J.; Izakovic, M.; Mazur, M.; Free radicals, metals and antioxidants in oxidative stress-induced cancer. Chem Biol Interact.; 160:1-40; 2006

3) Robbins, M. E.; Zhao, W.; Chronic oxidative stress and radiation-induced late normal tissue injury: a review. Int J Radiat Biol.; 80:251-259; 2004

4) Zhao, W.; Diz, D. I.; Robbins, M. E.; Oxidative damage pathways in relation to normal tissue injury. Br J Radiol. 80:23-31; 2007

5) Kalen, A. L.; Sarsour, E. H., Venkataraman, S.; Goswami, P. C.; Mn-superoxide dismutase overexpression enhances G2 accumulation and radioresistance in human oral squamous carcinoma cells. Antioxid Redox Signal. 8:1273-1281; 2006

6) Martin, R. C.; Ahn, J.; Nowell, S. A.; Hein, D. W.; Doll, M. A.; Martini, B. D. et al. Association between manganese superoxide dismutase promoter gene polymorphism and breast cancer survival. Breast Cancer Res; 8:R45; 2006

7) Stenlund, P. and Tibell, L. A. Chimeras of human extracellular and intracellular superoxide dismutases. Analysis of structure and function of the individual domains. Protein Eng; 12:319-325; 1999

8) Greenberger, J. S.; Epperly, M. W.; Gretton, J.; Jefferson, M.; Nie, S.; Bernarding, M.; Kagan, V.; and Guo, H. L. Radioprotective Gene Therapy. Curr Gene Ther.; 3:183-95; 2003

9) Mancini, A.; Borrelli, A.; Schiattarella, A.; Fasano, S.; Occhiello, A.; Pica, A.; Tommasino, M.; Nüesch, J. P. F.; and Rommelaere, J. Tumor Suppressive Activity of a Variant Isoform of Mn Superoxide Dismutase Released by a Human Liposarcoma Cell Line. Int. J. Cancer: 119, 932-943; 2006

10) Mancini, A.; Borrelli, A.; Schiattarella, A.; Aloj, L; Aurilio, M.; Morelli, F., Pica, A;. Occhiello, A; Lorizio, R.; Mancini, R; Sica, A; Mazzarella, L; Sica, F.; Grieco, P.; Novellino, E.; Pagnozzi, D; Pucci, P; and Rommelaere J. Biophysical and Biochemical Characterization of a Liposarcoma Derived Recombinant MnSOD Protein Acting as Anticancer Agent. Int. J. Cancer: 123, 2684-2695 (2008); 2008

11) McCord, J. M.; Fridovich, I.; Superoxide dismutase. An enzymic function for erythrocuprein (hemocuprein). J Biol. Chem.; 244:6049-55; 1969

12) Mancini A.; Garbi C.; D'Armiento, F.; Borrelli A.; and Ambesi-Impiombato F. S. Culture and cloning of an adipocytes cell line from a human liposarcoma. Bolletino dell'Istituto dei Tumori di Napoli.; 38:43-49; 1991

13) Franken, N. A.; Rodermond, H. M.; Stap, J.; Haveman, J.; van Bree, C. Clonogenic assay of cells in vitro. Nat. Protoc. 1; 2315-19; 2006

14) Biade, S.; Stobbe, C.; and Chapman J. D. The intrinsic radiosensitivity of some human tumor cells throughout their cell cycles. Radiat Res; 147: 416-421; 1997

15) Tucker, S. L.; Is the mean inactivation dose a good measure of cell radiosensitivity? Radiat Res; 105:18-26; 1986

16) Tucker, S. L. Parameters of radiosensitivity. Radiat Res.; 108:226-9; 1986

17) Fertil, B.; and Malaise, E. P. Intrinsic radiosensitivity of human cell lines is correlated with radioresponsiveness of human tumors: Analysis of 101 published survival curves. Int J Radiat Oncol Biol Phys; 11:1699-1707; 1985

18) Malaise, E. P. Fertil, B.; Chavaudra, N.; Guichard, M; Distribution of radiation sensitivities for human tumor cells of specific histological types: Comparison of in vitro to in vivo data. Int J Radiat Oncol Biol Phys; 12:617-624; 1986

19) Deschavanne, P. J.; Debieu, D.; Fertil, B.; Malaise, E. P.; Re-evaluation of in vitro radiosensitivity of human fibroblasts of different genetic origins. Int J Radiat Biol; 50 279-293; 1986.

20) Malaise, E. P.; Fertil B.; Deschavanne, P. J.; Chavaudra, N.; Brooks W. A. Initial slope of radiation survival curves is characteristic of the origin of primary anestablished cultures of human tumor cells and fibroblasts. Radiat. Res. 111, 319-333; 1987

21) Chomczynski, P.; Sacchi, N. The single-step method of RNA isolation by acid guanidinium thiocyanate-phenol-chloroform extraction: twenty-something years on. Nat. Protoc.; 1:581-5; 2006

22) Chung-man Ho, J.; Zheng, S.; Comhair, S. A.; Farver, C.; Erzurum, S. C. Differential expression of manganese superoxide dismutase and catalase in lung cancer. Cancer Res; 61:8578-85; 2001

23) Pljesa-Ercegovac, M.; Mimic-Oka, J.; Dragicevic, D.; Savic-Radojevic, A.; Opacic, M.; Pljesa, S.; Radosavljevic, R.; Simic, T. Altered antioxidant capacity in human renal cell carcinoma: role of glutathione associated enzymes. Urol Oncol.; 26:175-81; 2008

24) Greenberger, J. S.; Epperly, M. W. Antioxidant gene therapeutic approaches to normal tissue radioprotection and tumor radiosensitization. In Vivo.; 21:141-6; 2007

25) Epperly M. W.; Epstein, C. J.; Travis, E. L. and Greenberger J. S. Decreased Pulmonary Radiation Resistance of Manganese Superoxide Dismutase (MnSOD)-Deficient Mice Is Corrected by Human Manganese Superoxide Dismutase-Plasmid/Liposome (SOD2-PL) Intratracheal Gene Therapy. Radiation Research, 154:365-374; 2000

26) Dolgachev, V.; Oberley, L. W.; Huang, T. T.; Kraniak, J. M.; Tainsky, M. A.; Hanada, K.; Separovic, D. A role for manganese superoxide dismutase in apoptosis after photosensitization Biochem Biophys Res Commun.; 332:411-7; 2005.

27) Murley, J. S.; Kataoka, Y.; Cao, D.; Li, J. J.; Oberley, L. W.; Grdina D. J Delayed radioprotection by NF kappa B-mediated induction of Sod2 (MnSOD) in SA-NH tumor cells after exposure to clinically used thiolcontaining drugs. Radiat Res. 162:536-46; 2004

28) Yan, S.; Brown; S. L.; Kolozsvary, A.; Freytag, S. O.; Lu, M.; Kim, J. H. Mitigation of radiation-induced skin injury by AAV2-mediated MnSOD gene therapy. J Gene Med.; 10:1012-8; 2008

29) Chau, B. N.; Cheng, E. H.; Kerr, D. A.; Hardwick, J. M.; Aven, a novel inhibitor of caspase activation, binds Bcl-xL and Apaf-1. Mol Cell 6:31-40; 2000

30) Liu, X.; Kim, C. N.; Yang, J.; Jemmerson, R.; Wang, X. Induction of apoptotic program in cell-free extracts: requirement for dATP and cytochrome c, Cell 86:147-157; 1996

31) Bertini, I.; Cavallaro, G.; Rosato, A.; Cytochrome c: occurrence and functions. Chem. Rev. 106:90-115; 2006.

32) Bernard, D.; Gosselin, K.; Monte, D.; Vercamer, C.; Bouali, F.; Pourtier, A.; Vandenbunder, B.; Abbadie, C. Involvement of Rel/nuclear factor-transcriptor factors in keratinocytes senescence. Cancer res. 64:472-481; 2004.

The invention claimed is:

1. A method for protecting a subject from exposure to radiations comprising administering to said subject a daily amount of from 0.08 mg/Kg body weight to 0.1 g/Kg body weight of rMnSOD of SEQ ID NO:1 for at least 15 days before exposure to radiations.

2. The method according to claim 1, wherein said radiations are space radiations.

3. The method according to claim 1, wherein said radiations are sun radiations.

4. The method according to claim 1, wherein said radiations are from depleted uranium.

5. The method according to claim 1, wherein said radiations are from anti-tumoral metabolic therapies administration of radioactive isotopes.

6. The method according to claim 1, wherein said radiations are from radioactive isotopes for radio-diagnostics.

7. The method according to claim 1, wherein said radiations are ionizing and/or protonizing radiations.

8. A method for treating a subject exposed to radiations comprising administering to said subject a daily amount of from 0.08 mg/Kg body weight to 0.1 g/Kg body weight of rMnSOD of SEQ ID NO:1 for at least 6 days after exposure to radiations.

9. The method according to claim 8, wherein said radiations are space radiations.

10. The method according to claim 8, wherein said radiations are ionizing and/or protonizing radiations.

11. A method for protecting a subject from exposure to radiations comprising administering to said subject an amount of from 0.08 mg/Kg/body weight to 0.1 g/Kg body weight of rMnSOD of claim 1 while exposing said subject to radiations.

12. The method according to claim 11, wherein said radiations are space radiations.

13. The method according to claim 11, wherein said radiations are sun radiations.

14. The method according to claim 11, wherein said radiations are from depleted uranium.

15. The method according to claim 11, wherein said radiations are from anti-tumoral metabolic therapies administration of radioactive isotopes.

16. The method according to claim 11, wherein said radiations are from radioactive isotopes for radio-diagnostics.

17. The method according to claim 11, wherein said radiations are ionizing and/or protonizing radiations.

* * * * *

SEQUENCE LISTING

<160> NUMBER OF SEQ ID NOS: 5

<210> SEQ ID NO 1
<211> LENGTH: 222
<212> TYPE: PRT
<213> ORGANISM: Homo sapiens
<300> PUBLICATION INFORMATION:
<308> DATABASE ACCESSION NUMBER: P04179
<309> DATABASE ENTRY DATE: 1990-04-01
<313> RELEVANT RESIDUES IN SEQ ID NO: (1)..(222)

<400> SEQUENCE: 1

Met Leu Ser Arg Ala Val Cys Gly Thr Ser Arg Gln Leu Ala Pro Ala
1               5                   10                  15

Leu Gly Tyr Leu Gly Ser Arg Gln Lys His Ser Leu Pro Asp Leu Pro
            20                  25                  30

Tyr Asp Tyr Gly Ala Leu Glu Pro His Ile Asn Ala Gln Ile Met Gln
        35                  40                  45

Leu His His Ser Lys His His Ala Ala Tyr Val Asn Asn Leu Asn Val
    50                  55                  60

Thr Glu Glu Lys Tyr Gln Glu Ala Leu Ala Lys Gly Asp Val Thr Ala
65                  70                  75                  80

Gln Ile Ala Leu Gln Pro Ala Leu Lys Phe Asn Gly Gly Gly His Ile
                85                  90                  95

Asn His Ser Ile Phe Trp Thr Asn Leu Ser Pro Asn Gly Gly Gly Glu
            100                 105                 110

Pro Lys Gly Glu Leu Leu Glu Ala Ile Lys Arg Asp Phe Gly Ser Phe
        115                 120                 125

Asp Lys Phe Lys Glu Lys Leu Thr Ala Ala Ser Val Gly Val Gln Gly
    130                 135                 140

Ser Gly Trp Gly Trp Leu Gly Phe Asn Lys Glu Arg Gly His Leu Gln
145                 150                 155                 160

Ile Ala Ala Cys Pro Asn Gln Asp Pro Leu Gln Gly Thr Thr Gly Leu
                165                 170                 175

Ile Pro Leu Leu Gly Ile Asp Val Trp Glu His Ala Tyr Tyr Leu Gln
            180                 185                 190

Tyr Lys Asn Val Arg Pro Asp Tyr Leu Lys Ala Ile Trp Asn Val Ile
        195                 200                 205

Asn Trp Glu Asn Val Thr Glu Arg Tyr Met Ala Cys Lys Lys
    210                 215                 220

<210> SEQ ID NO 2
<211> LENGTH: 19
<212> TYPE: DNA
<213> ORGANISM: Artificial Sequence
<220> FEATURE:
<223> OTHER INFORMATION: primer

<400> SEQUENCE: 2
gaatctcagc ggggcacag                                               19

<210> SEQ ID NO 3
<211> LENGTH: 19
<212> TYPE: DNA
<213> ORGANISM: Artificial Sequence
<220> FEATURE:
<223> OTHER INFORMATION: primer

<400> SEQUENCE: 3

```
                                                   -continued
gggcaagcac cagcagcag                                                              19

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
gactacctca tgaagatcct                                                             20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
gcttgctgat ccacatctgc                                                             20
```